United States Patent
Prasad et al.

(10) Patent No.: US 11,857,647 B2
(45) Date of Patent: Jan. 2, 2024

(54) PHARMACEUTICAL COMPOSITION COMPRISING TETROFOSMIN AND PHARMACEUTICALLY ACCEPTABLE SALTS THEREOF

(71) Applicant: Jubilant Generics Limited, Noida (IN)

(72) Inventors: Umamaheshwar M. Prasad, Noida (IN); Harmik Sohi, Noida (IN); Rahul Hasija, Noida (IN); Dinesh Kumar, Noida (IN); Kamal S. Mehta, Noida (IN); Raj Vijaya Kuniyil Kulangara, Noida (IN); Ashutosh Agarwal, Noida (IN); Dharam Vir, Noida (IN)

(73) Assignee: Jubilant Draximage, Inc.

( * ) Notice: Subject to any disclaimer, the term of this patent is extended or adjusted under 35 U.S.C. 154(b) by 0 days.

(21) Appl. No.: 16/627,466

(22) PCT Filed: Nov. 22, 2018

(86) PCT No.: PCT/IB2018/059209
§ 371 (c)(1),
(2) Date: Dec. 30, 2019

(87) PCT Pub. No.: WO2019/102388
PCT Pub. Date: May 31, 2019

(65) Prior Publication Data
US 2021/0145987 A1    May 20, 2021

(30) Foreign Application Priority Data
Nov. 23, 2017  (IN) .............. 201711042108

(51) Int. Cl.
*A61K 51/04* (2006.01)
*A61K 9/19* (2006.01)
*A61K 31/66* (2006.01)
*A61K 51/02* (2006.01)

(52) U.S. Cl.
CPC ............ *A61K 51/0478* (2013.01); *A61K 9/19* (2013.01); *A61K 31/66* (2013.01); *A61K 51/025* (2013.01)

(58) Field of Classification Search
CPC .... A61K 9/19; A61K 51/0478; A61K 51/025; A61K 47/12; A61K 31/66; C07F 9/5027; C07F 13/005
See application file for complete search history.

(56) References Cited

U.S. PATENT DOCUMENTS

| 4,233,284 A | 11/1980 | Fawzi |
| 2004/0057899 A1 | 3/2004 | Forester et al. |
| 2010/0236958 A1 | 9/2010 | Veggeland et al. |

FOREIGN PATENT DOCUMENTS

EP    1824525 B1 *  4/2008  ............. A61K 51/04

OTHER PUBLICATIONS

Pervez et al., J Radioanal Nucl Chem, 2009, 281, p. 371-377. (Year: 2009).*

* cited by examiner

*Primary Examiner* — Michael G. Hartley
*Assistant Examiner* — Leah H Schlientz
(74) *Attorney, Agent, or Firm* — William D. Hare, Esq.; McNeely, Hare & War, LLP

(57) ABSTRACT

The present invention relates to a stable pharmaceutical composition of tetrofosmin or pharmaceutically acceptable salts thereof. It also relates to a lyophilized non-radioactive kit which upon reconstitution with $^{99m}$Tc-pertechnetate solution gives a stable $^{99m}$Tc-tetrofosmin radiopharmaceutical composition. It also provides process for the preparation of said radiopharmaceutical compositions and their use in diagnostic imaging procedures. The compositions provide desirable technical attributes such as stability, high radiochemical purity (RCP) and desired bio-distribution.

20 Claims, No Drawings

PHARMACEUTICAL COMPOSITION COMPRISING TETROFOSMIN AND PHARMACEUTICALLY ACCEPTABLE SALTS THEREOF

FIELD OF THE INVENTION

The present invention relates to a stable radiopharmaceutical composition of tetrofosmin or its pharmaceutically acceptable salts thereof. It also relates to a lyophilized non-radioactive kit which upon reconstitution with $^{99m}$Tc-pertechnetate solution gives a stable $^{99m}$Tc-tetrofosmin radiopharmaceutical composition. It also provides process for the preparation of said radiopharmaceutical compositions and their use for diagnostic purposes.

BACKGROUND OF THE INVENTION

Radiopharmaceuticals based on the technetium-99m ($^{99m}$Tc) are used in diagnostic nuclear medicine for in-vivo imaging. $^{99m}$Tc tetrofosmin injection is indicated for myocardial perfusion imaging to delineate regions of reversible myocardial ischemia or infarcted myocardium in patients with known or suspected coronary artery disease. Formulation is also used in the assessment of the left ventricular function.

Tetrofosmin is chemically known as 6, 9-bis (2-ethoxyethyl)-3, 12-dioxa-6, 9-diphospha-tetradecane (FIG. 1). It forms a lipophilic cationic complex with $^{99m}$Tc on addition of sodium pertechnetate $^{99m}$Tc solution (FIG. 2).

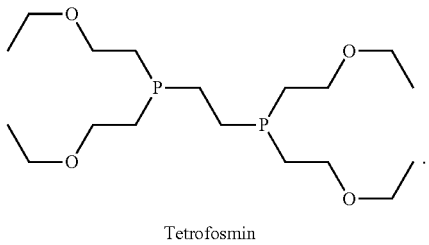

Tetrofosmin

FIG. 1

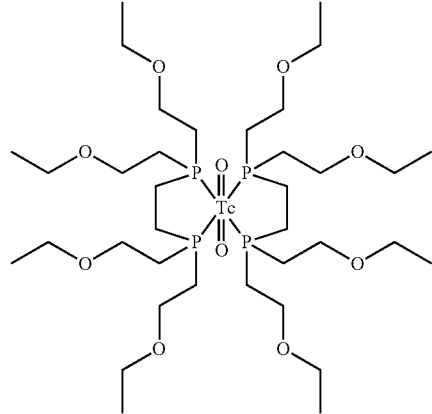

FIG. 2

Tetrofosmin is currently marketed as Myoview® 30 mL by GE Healthcare in the form of a lyophilized kit in the USA. The kit contains a pack of five multi-dose vials. Each vial contains sterile, non-pyrogenic, lyophilized mixture of tetrofosmin, stannous chloride dihydrate, disodium sulfosalicylate, sodium D-gluconate, sodium hydrogen carbonate and ascorbic acid. Formulation is used for the detection of reversible myocardial ischemia and myocardial infarction. The commercial preparation contains ascorbic acid as the sole radioprotectant.

U.S. Pat. No. 5,045,302 assigned to Amersham relates to tetrofosmin as a product. It discloses cationic complexes of the ligands with Technetium-99m useful for body imaging, particularly myocardial imaging.

U.S. Pat. No. 7,052,672 assigned to GE Healthcare pertains to Technetium ($^{99m}$Tc) based radiopharmaceutical composition with radio protectant consisting of ascorbic acid, para-aminobenzoic acid or gentisic acid along with parabens based antimicrobial preservatives. The use of preservatives was an essential feature of the invention which were required to suppress the growth of microorganisms and to obtain stable composition which can be stored at ambient or room temperature.

U.S. Patent publication No. US 2011/0008252 assigned to GE Healthcare discloses radiopharmaceutical compositions of tetrofosmin with ascorbic acid or ascorbate as a radio protectant without using antimicrobial preservative. The use of ascorbic acid is an essential feature of the invention.

U.S. Pat. No. 9,549,999 assigned to GE Healthcare discloses along with ascorbic acid or its salt where the ratio of tetrofosmin and ascorbic acid is in the range of 0.2:1.0 to 1.0:1.0. The formulation disclosed in the patent publications is stable at 2-8° C.

The commercial preparations of tetrofosmin comprise ascorbic acid as a radioprotectant which is important for their stability. The compositions which contain other radioprotectants require use of preservatives. However, the use of ascorbic acid as a radioprotectant is beset with challenges as ascorbic acid is known to be an unstable compound particularly in solution form and when exposed to UV light.

There exists a need in the art of radiopharmaceutical composition of tetrofosmin with desirable technical attributes such as stability, high radiochemical purity (RCP), desired bio-distribution and wherein manufacturing process is simple and reproducible process. The lyophilized composition and the reconstituted radiopharmaceutical composition should have an extended shelf-life.

The present inventors have surprisingly found that the exclusion of ascorbic acid and antimicrobial preservative offers desirable formulation characteristics like stability, radiochemical purity having desirable bio-distribution which is comparable to commercially available tetrofosmin compositions Myoview® 30 mL.

The present inventors have developed an improved compositions of tetrofosmin with desirable technical attributes such as stability, high radiochemical purity and desired bio-distribution.

Further, the process employed in the manufacture of lyophilized kit of tetrofosmin is simple, reproducible and suitable for industrial production and diagnostic use.

SUMMARY OF THE INVENTION

The present invention relates to a stable pharmaceutical composition of tetrofosmin or pharmaceutically acceptable salts thereof. It also relates to a lyophilized non-radioactive kit which upon reconstitution with $^{99m}$Tc-pertechnetate solution gives a stable $^{99m}$Tc-tetrofosmin radiopharmaceutical composition. It also provides process for the preparation of said radiopharmaceutical compositions and their use for diagnostic purposes. The compositions provide desirable technical attributes such as stability at room temperature, high radiochemical purity (RCP) and desired bio-distribu-

DETAILED DESCRIPTION OF THE INVENTION tion. The compositions of the present invention are manufactured by a simple and reproducible process which is suitable for industrial production.

As used herein, the term "Tetrofosmin" includes not only tetrofosmin per se but also its pharmaceutically acceptable salts such as tetrofosmin disulfosalicylate, tetrofosmin sulfosalicylate, tetrofosmin hydrobromide and tetrofosmin hydrochloride.

As used herein, the term "composition", as in pharmaceutical composition, is intended to encompass a diagnostic product comprising tetrofosmin or its pharmaceutically acceptable salts, and the other inert ingredient(s) (pharmaceutically acceptable excipients). Such pharmaceutical compositions are synonymous with "formulation" and "dosage form".

As used herein, the term "lyophilized kit", is intended to encompass a kit which comprises a freeze-dried composition comprising tetrofosmin or its pharmaceutically acceptable salts and one or more pharmaceutically acceptable excipients.

As used herein, the term "non-radioactive composition", as in pharmaceutical composition, is intended to encompass a freeze-dried composition comprising tetrofosmin or its pharmaceutically acceptable salts, and one or more pharmaceutically acceptable excipients.

As used herein, the term "radiopharmaceutical composition", as in pharmaceutical composition, is intended to encompass a composition comprising $^{99m}$Tc-pertechenetate solution, tetrofosmin or its pharmaceutically acceptable salts, and one or more pharmaceutically acceptable excipients.

As used herein, the term "excipient" means an inactive component i.e., which do not have diagnostic function such as a biocompatible reductant, transchelator, pH adjusting agent, filler, radioprotectant, and the like. The excipients that are useful in preparing a pharmaceutical composition are generally safe, non-toxic and are acceptable for human pharmaceutical use. Reference to an excipient includes both one and more than one such excipient. Combination of excipients performing the same function may also be used to achieve desired composition characteristics.

As used herein, the term "reductant or reducing agent" means a compound which is capable of reducing the technetium from a high oxidation state (such as Tc(VII)) to lower oxidation states of technetium. Suitable reductants as per the present invention include, but are not limited to, sodium dithionite, sodium bisulphite, formamidine sulphinic acid, tin, iron(II) or copper(I), sodium borohydride. Biocompatible reductant preferably comprises stannous ions, metallic tin or an alloy thereof in the form of Tin (II), and salts of Tin (II) such as stannous chloride dihydrate, stannous tartrate, stannous phosphate, stannous citrate etc.

As used herein, the term "transchelator" also referred to as transfer ligand or intermediate ligand, a compound which reacts rapidly with technetium to form a weak complex and is then displaced from this complex by the ligand and accordingly ensures reduced risk of formation of reduced hydrolyzed technetium (RHT) due to rapid reduction of pertechnetate competing with technetium complexation. Suitable transchelators are salts of organic acids with a biocompatible cation, particularly "weak organic acids" with a pKa in the range 3 to 7. Suitable such weak organic acids include, but are not limited to, gluconic acid, acetic acid, citric acid, tartaric acid, glucoheptonic acid, benzoic acid, phenols or phosphonic acids. Suitable salts are acetates, citrates, tartrates, gluconates, glucoheptonates, benzoates, phenolates or phosphonates. Two or more transchelators may be used in combination to achieve the desired results.

As used herein, the term "pH-adjusting agents" refers to a compound or mixture of compounds capable of maintaining the pH of the radiopharmaceutical composition within limits acceptable for human administration. Preferably pH of the radiopharmaceutical composition is about 4.0 to about 10. pH adjusting agents suitable for use in the present invention include, but are not limited to, pharmaceutically acceptable buffers such as tricine, phosphate or TRIS [tris (hydroxymethyl)aminomethane]; pharmaceutically acceptable bases such as sodium bicarbonate, sodium carbonate, or mixtures thereof.

As used herein, the term "filler" refers to bulking agent which eases handling of material during production of lyophilized kit or radiopharmaceutical composition.

As used herein, the term "radioprotectant" means a compound which prevents degradation reactions, such as redox reactions, by trapping highly reactive free radical species such as oxygen containing free radicals generated from the radiolysis of water. Radioprotectants of the present invention include, but are not limited to para-aminobenzoic acid, gentisic acid, maleic acid, anthranilic acid or their pharmaceutically acceptable salts thereof and combinations thereof.

As used herein, the term "about" means±approximately 20% of the indicated value, such that "about 10 percent" indicates approximately 8 to 12 percent.

"Biocompatible carrier" as used herein refers to a liquid in which the radiopharmaceutical is suspended or dissolved, such that the composition is physiologically tolerable. The biocompatible carrier can be an injectable carrier liquid such as sterile, pyrogen-free water for injection; an aqueous solution such as saline (which is isotonic); sugars (e.g. sucrose or glucose), sugar alcohols (e.g. mannitol or sorbitol), glycols (e.g. glycerol), or other non-ionic polyol materials (e.g. polyethyleneglycols, propylene glycols etc.). The biocompatible carrier may also comprise biocompatible organic solvents such as ethanol. Preferably, the biocompatible carrier is pyrogen-free water for injection or isotonic saline.

As used herein, the term "radiochemical purity" refers to proportion of the total radioactivity in the sample which is present as the desired radiolabelled product. The radiochemical purity can be measured in curie, millicurie, becqurels.

As used herein, the term "HPLC" refers high performance Liquid chromatography used to measure content of various components in a sample using US Pharmacopeial methods.

As used herein, the term "GC" refers gas chromatography used to measure content of various components in a sample using US Pharmacopeial methods.

As used herein, the term "TGA refers Thermo Gravimetric Analysis used to measure content of various components in a sample using US Pharmacopeial methods.

In one aspect, the present invention provides a stable radiopharmaceutical composition comprising tetrofosmin or its pharmaceutically acceptable salts thereof with one or more pharmaceutically acceptable excipients, wherein the composition does not contain ascorbate or ascorbic acid as a radioprotectant.

In yet another aspect of the present invention provides a stable radiopharmaceutical composition comprising tetrofosmin or its pharmaceutically acceptable salts and one or more pharmaceutically acceptable excipients, with the proviso that the radioprotectant is not ascorbic acid. The radioprotectant according to the present invention is selected from the group consisting of gentisic acid, para-amino benzoic acid, maleic acid, anthranilic acid, or their pharmaceutically acceptable salts thereof and combinations thereof, wherein the composition is free of antimicrobial preservatives.

In yet another aspect of the present invention provides a lyophilized, non-radioactive kit which upon reconstitution with $^{99m}$Tc-pertechnetate solution gives a stable $^{99m}$Tc-tetrofosmin radiopharmaceutical composition comprising (i) tetrofosmin or its pharmaceutically acceptable salts and one or more pharmaceutically acceptable excipients and (ii) a vial containing $^{99m}$Tc-pertechnetate.

According to one embodiment of this aspect, the kit is unit dose or multi dose. In one aspect, the non-radioactive kit comprises (i) first container containing tetrofosmin or pharmaceutically acceptable salts, reductants, transchelator, radioprotectant selected from gentisic acid, para amino benzoic acid, benzoic acid, maleic acid, anthranilic acid optionally preservative other than parabens (ii) second container comprising buffer, pH adjusting agents, transchelator, diluents, fillers, solvents or other pharmaceutically acceptable excipients.

According to one embodiment of the above aspects, wherein the pharmaceutically acceptable excipients are selected from the group comprising biocompatible reductant, transchelator, pH adjusting agent, filler and radio protectant selected from the group consisting of gentisic acid, para-amino benzoic acid, maleic acid, anthranilic acid or their pharmaceutically acceptable salts thereof or combinations thereof.

According to one aspect of the present invention, the non-radioactive composition comprises tetrofosmin or its pharmaceutically acceptable salts; a radio protectant selected from group consisting of gentisic acid, maleic acid, para amino benzoic acid, anthranilic acid; a transchelator selected from gluconic acid, acetic acid, citric acid, tartaric acid, glucoheptonic acid, benzoic acid, phenol or phosphonic acid or their pharmaceutically acceptable salts thereof and combinations thereof; wherein the composition is free of ascorbic acid and antimicrobial preservatives.

According to another aspect of the present invention, the radiopharmaceutical composition comprises a (a) $^{99m}$Tc complex of tetrofosmin; (b) tetrofosmin or its pharmaceutically acceptable salts thereof selected from sulfosalcylate, disulfosalcylate; (c) at least one or more radio protectant selected from group consisting of gentisic acid, maleic acid, para amino benzoic acid, anthranilic acid or their pharmaceutically acceptable salts or combinations thereof; (d) at least one or more transchelator selected from gluconic acid, acetic acid, citric acid, tartaric acid, glucoheptonic acid, benzoic acid, phenol or phosphonic acid or their pharmaceutically acceptable salts thereof and combinations thereof; (e) a reducing agent such as stannous chloride dihydrate, stannous tartrate, stannous phosphate, stannous citrate; wherein the composition is free of ascorbic acid and antimicrobial preservative.

In another aspect of the present invention, a process for producing a lyophilized composition, useful for diagnostic imaging, comprising the steps of:

(a) preparing an aqueous solution of tetrofosmin or pharmaceutically acceptable salts;

(b) addition of at least one or more radioprotectant selected from the group consisting of, gentisic acid, maleic acid, para amino benzoic acid, anthranilic acid or their pharmaceutically acceptable salts;

(c) addition of at least one or more reducing agent such as stannous chloride dihydrate, stannous tartrate, stannous phosphate, stannous citrate or their pharmaceutically acceptable salts thereof;

(d) addition of at least one or more transchelator selected from gluconic acid, acetic acid, citric acid, tartaric acid, glucoheptonic acid, benzoic acid, phenol or phosphonic acid or their pharmaceutically acceptable salts thereof;

(e) lyophilizing said solution.

In one aspect of the present invention, the radiopharmaceutical composition comprises $^{99m}$Tc complex of tetrofosmin; tetrofosmin or its pharmaceutically acceptable salts thereof selected from sulfosalicylate, disulfosalcylate, hydrobromide, hydrochloride; a radio protectant selected from group consisting of gentisic acid, maleic acid, para amino benzoic acid, anthranilic acid or their pharmaceutically acceptable salts thereof and combinations thereof; wherein the composition is free of ascorbate or ascorbic acid; a transchelator selected from gluconic acid, acetic acid, citric acid, tartaric acid, glucoheptonic acid, benzoic acid, phenol or phosphonic acid or their pharmaceutically acceptable salts thereof; wherein the composition has a radiochemical purity of at least 90% after 12 hours of storage at temperature 2-30° C.

In yet another aspect of the present invention provides a process for the preparation of multiple unit patient doses of radiopharmaceutical composition of tetrofosmin comprising: reconstituting the lyophilized composition with either a sterile solution of $^{99m}$Tc-pertechnetate or first a biocompatible carrier followed by a sterile solution of $^{99m}$Tc-pertechnetate to obtain desired $^{99m}$Tc-tetrofosmin radiopharmaceutical to be withdrawn into a clinical grade container to obtain desired doses when required.

In an another aspect of the present invention, provides use of a stable radiopharmaceutical composition comprising tetrofosmin or its pharmaceutically acceptable salts and one or more pharmaceutically acceptable excipients in the scintigraphic delineation of regions of reversible myocardial ischemia in the presence or absence of infarcted myocardium and for the evaluation of ventricular function.

In an embodiment a stable non-radiopharmaceutical composition comprising tetrofosmin or its pharmaceutically acceptable salts thereof and gentisic acid as radioprotectant characterized in that said composition retains at least 95% w/w of total tetrofosmin after storage at temperature 2-30° C. for at least three months, preferably five months, more preferably six months.

In an embodiment a radiopharmaceutical composition comprises (i) a $^{99m}$Tc complex of tetrofosmin; (ii) tetrofosmin disulfosalcylate (iii) gentisic acid as radioprotectant; wherein the molar ratio of tetrofosmin to gentisic acid is in the range 0.01:1.0 to 1.0:1.0.

In an embodiment a stable non-radiopharmaceutical composition comprising tetrofosmin, gentisic acid, wherein the molar ratio of tetrofosmin to gentisic acid is in the range 0.01:1.0 to 1.0:1.0 characterized in that said composition retains at least 95% w/w of total tetrofosmin after storage at temperature 2-30° C. for at least six months.

In an another aspect, the present invention provides a tetrofosmin composition after reconstitution with $^{99m}$Tc-pertechnetate which has a radiochemical purity of at least 90% after 12 hours of storage at temperature 2-30° C.

In an another aspect, the present invention provides a tetrofosmin composition after reconstitution with $^{99m}$Tc-pertechnetate which has a radiochemical purity of at least 90% after 12 hours after storage of composition at temperature 2-30° C. for six months.

In an embodiment a stable non-radioactive composition comprising tetrofosmin or its pharmaceutically acceptable salts thereof, gentisic acid, wherein the composition is stable at room temperature for at least six months.

In an embodiment a stable lyophilized tetrofosmin composition comprises tetrofosmin or its pharmaceutically acceptable salts thereof having moisture content of less than 10%.

In accordance with still another embodiment of the present invention, there is provided a suitable clinical grade container or vial or pre-filled syringes or ampoules that are suitable for safe administration to patients.

In another embodiment of the invention, the stable non-radioactive composition comprising tetrofosmin or its pharmaceutically acceptable salt thereof, wherein the composition comprises one or more reducing agent. Reducing agents like stannous are susceptible to oxidation or hydrolysis hence, the composition comprising such agents also become susceptible to oxidation.

In one embodiment of the present invention the compositions are prepared in controlled environment using inert gas. The final lyophilized compositions are prepared in such a controlled atmosphere that lyophilized vial comprises less than 5 percent of oxygen content in vial head space. Maintaining an appropriate level of stannous in the composition is important for reducing technetium to lower oxidation state which is required for complexation with tetrofosmin.

In another embodiment, the present invention provides a stable pharmaceutical composition comprising less than 5% of the oxygen content in the vial head space.

The headspace gas above the composition in the vial is suitably an inert gas. By the term "inert gas" is meant a gas which would be used to provide an "inert atmosphere' to the composition. Such a gas does not undergo chemical reactions with organic compounds and is hence compatible with a wide range of synthetic compounds even on prolonged storage over many hours or even weeks in contact with the gas. Suitable gases include but not limited to helium, neon, argon, nitrogen, carbon dioxide or combinations thereof.

Each vial of composition includes tetrofosmin or its pharmaceutically acceptable salts from about 0.1 mg to about 50 mg.

In yet another embodiment, the present invention relates to stable non-radioactive composition comprising tetrofosmin or its pharmaceutically acceptable salt, wherein the amount of reducing agent in the radiopharmaceutical composition is in a molar excess to a $^{99m}$Tc-compound. Preferably, the reductant used in the present invention is between about 0.01% to about 15% (w/w).

Another embodiment of the present invention encompasses a stable non-radioactive composition comprising tetrofosmin or its pharmaceutically acceptable salt and a pharmaceutically acceptable transchelator. Combination of transchelators performing the same function may also be used to achieve desired formulation characteristics.

In another embodiment, the present invention includes a stable non-radioactive composition comprising tetrofosmin or its pharmaceutically acceptable salt, wherein the composition comprises one or more pharmaceutically acceptable pH-adjusting agents such as tricine, phosphate or TRIS [tris(hydroxymethyl)aminomethane]; pharmaceutically acceptable bases such as sodium bicarbonate, sodium carbonate, or mixtures thereof.

In another embodiment, the present invention includes a stable non-radioactive composition comprising tetrofosmin or its pharmaceutically acceptable salt, wherein the pH ranges from about 4.0 to 10.0.

The stable radiopharmaceutical composition comprising tetrofosmin or its pharmaceutically acceptable salt, is provided in either a suitable clinical grade container like vial or pre-filled syringes that are suitable for safe administration in patients. The pre-filled syringe may optionally be provided with a syringe shield to protect the operator from radioactive dose.

The stable radiopharmaceutical composition comprising tetrofosmin or its pharmaceutically acceptable salt, is compatible with clinical grade container closure system.

The present invention provides non-radioactive kits for the preparation of the stable $^{99m}$Tc radiopharmaceutical composition. Such kits comprise conventional non-radioactive freeze-dried vials containing the necessary reactants and are intended to be reconstituted with $^{99m}$Tc-pertechnetate (TcO4$^-$) from a supply of $^{99m}$Tc to give the desired sterile $^{99m}$Tc radiopharmaceutical composition. The compositions according to the present invention comprises a radioactivity of 1 mCi to 2400 mCi.

In a separate embodiment, the present invention relates to non-radioactive kits for the preparation of the stable $^{99m}$Tc radiopharmaceutical composition, wherein the kits comprise: (i) non-radioactive freeze-dried vial containing tetrofosmin, reductant and transchelator; buffering agent, radio protectant; (ii) vial containing $^{99m}$Tc-pertechnetate (TcO$_4$—) from a supply of $^{99m}$Tc.

In yet another independent embodiment, the present invention relates to the use of stable radiopharmaceutical composition comprising tetrofosmin or its pharmaceutically acceptable salt in the scintigraphic delineation of regions of reversible myocardial ischemia in the presence or absence of infarcted myocardium and for the evaluation of ventricular function. The composition as per present invention can be used for diagnosis of other organs also.

Having described the invention with reference to certain preferred embodiments, other embodiments will become apparent to one skilled in the art from consideration of the specification. The invention is further defined by reference to the following examples describing in detail method for the preparation of radiopharmaceutical compositions comprising tetrofosmin. It will be apparent to those skilled in the art that many modifications, both to materials and methods, may be practiced without departing from the scope of the invention. Following examples are set out to illustrate the invention and do not limit the scope of the invention.

EXAMPLES

The following examples are intended to further illustrate certain preferred embodiments of the invention and are not limiting in nature Example 1: Lyophilized Composition Per Vial Comprising Tetrofosmin is Given in Table 1

TABLE 1

| | Amount (% w/w) | | | |
| --- | --- | --- | --- | --- |
| Ingredients | Example A | Example B | Example C | Example D |
| Tetrofosmin Disulfosalicylate | 13.00-15.00 | 13.14-14.53 | 14.72 | 14.19 |
| Stannous Chloride Dihydrate | 0.37-0.5 | 0.37-0.46 | 0.44 | 0.43 |
| Sodium D-Gluconate | 12.00-16.00 | 12.65-15.47 | 14.97 | 14.43 |

TABLE 1-continued

| Ingredients | Amount (% w/w) | | | |
|---|---|---|---|---|
| | Example A | Example B | Example C | Example D |
| Sodium Bicarbonate | 50.00-62.00 | 50.59-61.84 | 54.89 | 52.91 |
| Gentisic Acid* | 15.00-17.00 | 13.54-15.00 | 14.97 | 18.03 |

*Para-amino benzoic acid, Maleic acid, Anthranilic acid can also be used

Procedure:

Approximately 90% of the total volume of Water for Injection (WFI) was added to a preparation vessel. The WFI was deoxygenated. Tetrofosmin, reducing agent selected from stannous chloride dihydrate, transchelator selected from Sodium D-gluconate, radioprotectant selected from Gentisic acid, para-amino benzoic acid, maleic acid, anthranilic acid and combinations thereof and sodium hydrogen carbonate were dissolved. The solution obtained was deoxygenated and final volume and the bulk solution was deoxygenated. The solution was sterile filtered. The vials were partially stoppered and then lyophilized.

Example 2: Radiolabelling Procedure

Test vial was placed in a suitable lead pot and stored under a mild atmosphere of nitrogen. A sterile venting needle was inserted through the rubber septum. Up to 2.4 Ci of technetium $^{99m}$Tc generator eluate diluted with about 15.0 mL sodium chloride injection was injected into the vial. Before removing the syringe from the vial, 2 mL of gas was withdrawn from above the solution and then the venting needle was removed. The contents of the vial were mixed gently to ensure complete solubilization of the powder and incubated at room temperature for 15 minutes. RCP was checked at 30 minutes and 12 hrs. The reconstituted product was stored at temperature 2-8° C. for 12 hrs.

Example 3: Radiochemical Purity Analysis by Ascending Paper Chromatography

RCP of the reconstituted test formulations and the marketed formulation (Myoview® 30 mL) were measured using two chromatographic systems System 1: Stationary phase: ITLC-SA (1×10 cm strip); Mobile phase: acetone and dichloromethane (65:35))]

System 2: Stationary phase: ITLC-SG (2×20 cm strip); Mobile phase: acetone and dichloromethane (65:35))

Method: To determine the amount of free technetium, a 10 to 20 µL volume of injection was applied about 1.0 cm from the bottom of a non-heated 1×10-cm glass fiber paper impregnated with silicic acid strip (ITLC-SA/ITLC-SG). The chromatogram was immediately developed by ascending chromatography using a solvent system consisting of a mixture of acetone and dichloromethane (65:35). The chromatogram was allowed to air-dry. The radioactivity distribution of the chromatogram was determined by scanning with Bioscan. The relative front (RF) value, which is defined as the ratio of component position to the total distance travelled by the solvent front, of the technetium $^{99m}$Tc tetrofosmin spot was found approximately at 0.5. The RCP based on the % ROI (region of interest) was recorded on the Bioscan report. The results of test formulation Example A and B are illustrated in Table 2:

TABLE 2

| Test Formulation | Radiochemical Purity of $^{99m}$Tc Tetrofosmin (%) | | |
|---|---|---|---|
| | Activity added | 30 minutes | 12 hour |
| Example A | 1.0 Ci | 97.45 | 94.63 |
| | 257 mCi | 98.49 | 98.43 |
| Example B | 2.21 Ci | 100 | 95.4 |
| | 2.01 Ci | 99.64 | 95.35 |
| Myoview ® (30 mL) | 1.86 Ci | 97.12 | 92.96 |

Radiochemical purity of test composition of Example C was compared with commercially available Myoview (30 mL) stored at temperature 2-8° C. for six months. The results are illustrated in Table 3.

TABLE 3

| | Stored at 2-8° C. | |
|---|---|---|
| Composition | Time post labelling | Radio chemical purity (%) |
| Myoview | 1 hour | 90.3 |
| | 12 hour | 87.2 |
| Example C (6 Month) | 1 hour | 99.0 |
| | 12 hour | 95.5 |

It is apparent from the above results that compositions according to the present invention provide superior radiochemical purity in comparison to the commercially available Myoview® (30 mL) compositions.

Example 5: Animal Bio-Distribution Data

Bio-distribution was determined after technetium-99m labeling of composition of Example A. Aliquots of solution were intravenously injected into tail vein of rats. % Injected dose (ID)/organ were determined at 10 minutes, 1 hour, 2 hours and 4 hours post injection.

Table 4 shows the comparison of Bio-distribution (10 minutes post injection) in animals between test formulation (Example A) and commercial formulation (Myoview®). Table 5 shows the comparison of Bio-distribution (1 hour post injection) in animals between test formulation (Example A) and commercial formulation. Table 6 shows the comparison of Bio-distribution (2 hour post injection) in animals between test formulation (Example A) and commercial formulation. Table 7 shows the comparison of Bio-distribution (4 hour post injection) in animals between test formulation (Example A) and commercial formulation.

TABLE 4

| Test Formulation and Myoview ® Bio-distribution (10 minutes post injection) | | |
|---|---|---|
| | % ID/organ | |
| Organ | Example A | Myoview ® |
| Blood | 0.78 | 0.76 |
| Liver | 7.86 | 5.42 |
| Kidneys | 7.63 | 5.83 |
| Stomach | 1.64 | 1.39 |
| Intestines | 18.85 | 19.83 |
| Muscle | 0.33 | 0.28 |
| Spleen | 0.99 | 0.95 |

TABLE 4-continued

Test Formulation and Myoview ® Bio-distribution
(10 minutes post injection)

| Organ | % ID/organ | |
|---|---|---|
| | Example A | Myoview ® |
| Lung | 1.09 | 1.27 |
| Heart | 1.84 | 1.54 |

TABLE 5

Test Formulation and Myoview ® Bio-distribution
(1 hour post injection)

| Organ | % ID/organ | |
|---|---|---|
| | Example A | Myoview ® |
| Blood | 0.34 | 0.32 |
| Liver | 2.69 | 1.95 |
| Kidneys | 3.53 | 2.45 |
| Stomach | 1.14 | 0.94 |
| Intestines | 33.61 | 26.3 |
| Muscle | 0.45 | 0.36 |
| Spleen | 0.53 | 0.37 |
| Lung | 0.81 | 0.91 |
| Heart | 1.94 | 1.49 |

TABLE 6

Test Formulation and Myoview ® Bio-distribution
(2 hours post injection)

| Organ | % ID/organ | |
|---|---|---|
| | Example A | Myoview ® |
| Blood | 0.2 | 0.21 |
| Liver | 1.44 | 1.21 |
| Kidneys | 2.35 | 1.65 |
| Stomach | 0.92 | 0.79 |
| Intestines | 35.29 | 27.01 |
| Muscle | 0.33 | 0.31 |
| Spleen | 0.28 | 0.17 |
| Lung | 0.5 | 0.75 |
| Heart | 1.53 | 1.06 |

TABLE 7

Test Formulation and Myoview ® Bio-distribution
(4 hours post injection)

| Organ | % ID/organ | |
|---|---|---|
| | Example A | Myoview ® |
| Blood | 0.15 | 0.16 |
| Liver | 0.71 | 0.97 |
| Kidneys | 1.06 | 1.17 |
| Stomach | 0.53 | 0.63 |
| Intestines | 33.7 | 39.81 |
| Muscle | 0.32 | 0.23 |
| Spleen | 0.11 | 0.1 |
| Lung | 0.34 | 0.64 |
| Heart | 1.29 | 1.41 |

It is apparent from the above results that test formulations according to the present invention provide comparable bio-distribution with respect to the commercially available Myoview® (30 mL) compositions.

Example 6

Lyophilized test formulation prepared in Example C was subjected to stability testing at temperature of 5°±3° C. for 6 months and content of tetrofosmin and gentisic acid was analyzed by High Performance Liquid Chromatography (HPLC) method, whereas content of stannous chloride dihydrate was measured by voltammeter, headspace oxygen content by Gas Chromatography and water content was analyzed by Thermo Gravimetric Analysis (TGA). The prepared dosage form was found to be stable and exhibited following values (refer Table 8):

TABLE 8

| Test Parameters | Acceptable limits | Stored at 5° C. ± 3° C. | | | |
|---|---|---|---|---|---|
| | | Initial (%) | 1 Month (%) | 3 Months (%) | 6 Months (%) |
| Assay of tetrofosmin | 90%-110% | 100.1 | 99.1 | 103.5 | 101.9 |
| Content of Stannous Chloride Dihydrate | NLT 32% | 92.1 | 91.4 | 89.4 | 89 |
| Headspace Oxygen (%) | NMT 2% | 0.2 | 1.0 | 0.6 | 0.6 |

Example 7

Lyophilized formulation prepared in Example D was subjected to stability testing at temperature of 5°±3° C. for 3 months (refer Table 9) and 25° C./60% RH for 1 month (refer Table 10). The content of tetrofosmin and gentisic acid was analyzed by High Performance Liquid Chromatography (HPLC) method, whereas content of stannous chloride dihydrate was measured by voltammeter, headspace oxygen content by GC and water content was analyzed by TGA. The prepared dosage form was found to be stable and exhibited following values. The prepared dosage form was found to be stable and exhibited following values (refer Table 9 and 10):

TABLE 9

| Test Parameters | Stored at 5° C. ± 3° C. | | |
|---|---|---|---|
| | Initial (%) | 1 Month (%) | 3 Months (%) |
| Assay of tetrofosmin | 105.4 | 100.9 | 102.2 |
| Content of Stannous Chloride Dihydrate | 84.3 | 84.9 | 83.7 |
| Content of Gentisic Acid | 100.8 | 100.5 | 99.9 |
| Headspace Oxygen (%) | 0.54 | 0.62 | 0.66 |
| Water content | 6.2 | 4.5 | 5.9 |

TABLE 10

| Test Parameters | Stored at 25° C./60% RH | |
|---|---|---|
| | Initial (%) | 1 Month (%) |
| Assay of tetrofosmin | 105.4 | 101.4 |
| Content of Stannous Chloride Dihydrate | 84.3 | 83.0 |

TABLE 10-continued

| | Stored at 25 °C./60% RH | |
|---|---|---|
| Test Parameters | Initial (%) | 1 Month (%) |
| Content of Gentisic Acid | 100.8 | 100.4 |
| Headspace Oxygen (%) | 0.54 | 0.59 |
| Water content | 6.2 | 4.9 |

Example 8

Lyophilized formulation prepared in Example B was subjected to stability testing at 25° C./60% RH for 6 months and content of tetrofosmin was analyzed by High Performance Liquid Chromatography (HPLC) method, whereas content of stannous chloride dihydrate was measured by voltammeter. The prepared dosage form was found to be stable and exhibited following assay values (refer Table 11):

TABLE 11

| | | Stored at 25 °C./60% RH | |
|---|---|---|---|
| Test Parameters | Acceptable limits | Initial | 6 Months |
| Assay of tetrofosmin | 90%-110% | 101.7% | 100.3% |
| Content of Stannous Chloride Dihydrate | NLT 32% | 83.6% | 81.6% |

While this invention has been described in detail with reference to certain preferred embodiments, it should be appreciated that the present invention is not limited to those precise embodiments. Rather, in view of the present disclosure, which describes the current best mode for practicing the invention, many modifications and variations would present themselves to those skilled in the art without departing from the scope, and spirit of this invention.

We claim:

1. A reconstituted radiopharmaceutical composition comprising:
   i) a first component comprising an aqueous solution of $^{99m}$Tc pertechnetate; and
   ii) a second component comprising:
   a) tetrofosmin disulfosalicylate in an amount between about 13.0-15.0% (w/w) of the second component;
   b) gentisic acid in an amount between about 13.54-18.03% (w/w) of the second component;
   c) a reducing agent in an amount between about 0.37-0.5% (w/w) of the second component;
   d) a transchelator in an amount between about 12.0-16.0% (w/w) of the second component; and
   e) sodium bicarbonate at an amount between about 50.0-62.0% (w/w) of the second component,
   wherein the tetrofosmin disulfosalicylate and reducing agent are present in a ratio by weight of about 30:1 to about 35:1,
   wherein the reconstituted radiopharmaceutical composition is free of ascorbate or ascorbic acid and an antimicrobial preservative, and
   the reconstituted radiopharmaceutical composition is reconstituted from the first component and second component, and has a radiochemical purity of at least 90% after 12 hours of storage at a temperature of 2-30° C.

2. The reconstituted radiopharmaceutical composition of claim 1, wherein the molar ratio of tetrofosmin disulfosalicylate to gentisic acid is in the range 0.01:1.0 to 1.0:1.0.

3. The reconstituted radiopharmaceutical composition of claim 1, wherein the composition has a radiochemical purity of at least 90% after storage of the second component at a temperature of 2-30° C. for 6 months.

4. The reconstituted radiopharmaceutical composition according to claim 1, wherein the second component prior to reconstitution retains at least 95% w/w of total tetrofosmin disulfosalicylate after storage at 2-30° C. for at least 3 months.

5. The reconstituted radiopharmaceutical composition according to claim 1, wherein the second component prior to reconstitution is contained within a vial having a vial head space that comprises an oxygen content of less than 5 percent in the vial head space.

6. The radiopharmaceutical composition according to claim 1, wherein the composition comprises a level of radioactivity in the range of 1 mCi to 2400 mCi.

7. A reconstituted radiopharmaceutical composition according to claim 1, wherein the reconstituted radiopharmaceutical composition is prepared by a process comprising the steps of:
   (a) preparing a first solution which comprises tetrofosmin disulfosalicylate;
   (b) adding gentisic acid to the first solution;
   (c) adding at least one or more reducing agent selected from the group consisting of stannous chloride dihydrate, stannous tartrate, stannous phosphate, stannous citrate or their pharmaceutically acceptable salts thereof to the first solution;
   (d) adding at least one or more transchelator selected from gluconic acid, acetic acid, citric acid, tartaric acid, glucoheptonic acid, or phosphonic acid or their pharmaceutically acceptable salts thereof and combinations thereof; and sodium bicarbonate to the first solution;
   (e) lyophilizing said first solution to form a lyophilate;
   (f) preparing an aqueous solution of $^{99m}$Tc pertechnetate; and
   (g) mixing the lyophilate with the aqueous solution of $^{99m}$Tc pertechnetate to form the reconstituted radiopharmaceutical composition.

8. The reconstituted radiopharmaceutical composition according to claim 7, wherein the lyophilate is enclosed within a container selected from vials, syringes, ampoules, and pre-filled syringes that are suitable for safe administration in patients.

9. The reconstituted radiopharmaceutical composition of tetrofosmin of claim 7, wherein the reconstituted radiopharmaceutical composition has a molar ratio of tetrofosmin disulfosalicylate to gentisic acid is 0.01:1.0 to 1.0:1.0.

10. The reconstituted radiopharmaceutical composition according to claim 1, wherein the second component comprises stannous chloride dihydrate as a reducing agent present in an amount between about 0.37-0.5% (w/w).

11. The reconstituted radiopharmaceutical composition according to claim 1, wherein the second component comprises sodium gluconate as a transchelator at an amount of about 12.0-16.0% (w/w).

12. The reconstituted radiopharmaceutical composition according to claim 10, wherein the second component comprises tetrofosmin disulfosalicylate present in an amount of about 14.72% (w/w), gentisic acid present in an amount of about 14.97% (w/w), stannous chloride dihydrate present in an amount of about 0.44% (w/w), sodium gluconate present in an amount of 14.97% (w/w) and sodium bicarbonate present in an amount of about 54.89% (w/w).

13. The reconstituted radiopharmaceutical composition of claim 1, wherein prior to reconstitution the first component comprises a sterile solution of $^{99m}$Tc-pertechnetate.

14. The reconstituted radiopharmaceutical composition according to claim 12, wherein the second component consists of tetrofosmin disulfosalicylate present in an amount of about 14.72% (w/w), gentisic acid present in an amount of about 14.97% (w/w), stannous chloride dihydrate present in an amount of about 0.44% (w/w), sodium gluconate present in an amount of 14.97% (w/w) and sodium bicarbonate present in an amount of about 54.89% (w/w).

15. The reconstituted radiopharmaceutical composition according to claim 10, wherein the ratio of the tetrofosmin disulfosalicylate to stannous chloride dihydrate is about 30:1 to about 35:1.

16. The reconstituted radiopharmaceutical composition according to claim 10, wherein the ratio of the tetrofosmin disulfosalicylate to stannous chloride dihydrate is about 30:1.

17. The reconstituted radiopharmaceutical composition according to claim 10, wherein the ratio of the tetrofosmin disulfosalicylate to stannous chloride dihydrate is about 35:1.

18. A liquid radiopharmaceutical composition consisting of:
a first component consisting of a saline solution of $^{99m}$Tc pertechnetate and water; and
a second component consisting of (i) tetrofosmin disulfosalicylate in an amount between about 13.0-15.0% (w/w) of the second component; (ii) gentisic acid in an amount between about 13.54-18.03% (w/w) of the second component; (iii) stannous chloride dihydrate in an amount between about 0.37-0.5% (w/w) of the second component; (iv) a transchelator in an amount between about 12.0-16.0% (w/w) of the second component; and (v) sodium bicarbonate at an amount between about 50.0-60.0% (w/w) of the second component,
wherein the tetrofosmin disulfosalicylate and stannous chloride dihydrate are present in a ratio by weight of about 30:1 to about 35:1,
wherein the liquid radiopharmaceutical composition is free of ascorbate or ascorbic acid and an antimicrobial preservative, and has a radiochemical purity of at least 90% after 12 hours of storage at a temperature of 2-30° C.

19. The liquid radiopharmaceutical composition of claim 18, wherein (i) the tetrofosmin disulfosalicylate is present in an amount of about 14.72% (w/w) of the second component; (ii) the gentisic acid is present in an amount of about 14.97% (w/w) of the second component; (iii) the stannous chloride dihydrate is present in an amount of about 0.44% (w/w) of the second component; (iv) the transchelator is sodium gluconate present in an amount of 14.97% (w/w) of the second component; and (v) the sodium bicarbonate present in an amount of about 54.89% (w/w) of the second component.

20. The liquid radiopharmaceutical composition of claim 18, wherein (i) the tetrofosmin disulfosalicylate is present in an amount of about 14.19% (w/w) of the second component; (ii) the gentisic acid is present in an amount of about 18.03% (w/w) of the second component; (iii) the stannous chloride dihydrate is present in an amount of about 0.43% (w/w) of the second component; (iv) the transchelator is sodium gluconate present in an amount of 14.43% (w/w) of the second component; and (v) the sodium bicarbonate present in an amount of about 52.91% (w/w) of the second component.

* * * * *